US012046350B2

(12) United States Patent
Neumann

(10) Patent No.: US 12,046,350 B2
(45) Date of Patent: Jul. 23, 2024

(54) METHODS AND SYSTEMS FOR CALCULATING AN EDIBLE SCORE IN A DISPLAY INTERFACE

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 413 days.

(21) Appl. No.: 17/007,227

(22) Filed: Aug. 31, 2020

(65) Prior Publication Data

US 2022/0036998 A1 Feb. 3, 2022

Related U.S. Application Data

(63) Continuation-in-part of application No. 16/983,034, filed on Aug. 3, 2020, now Pat. No. 11,688,506.

(51) Int. Cl.
*G16H 20/60* (2018.01)
*G16H 10/20* (2018.01)

(52) U.S. Cl.
CPC .............. *G16H 20/60* (2018.01); *G16H 10/20* (2018.01)

(58) Field of Classification Search
None
See application file for complete search history.

(56) References Cited

U.S. PATENT DOCUMENTS

| | | | |
|---|---|---|---|
| 8,647,121 B1* | 2/2014 | Witlin ................ | G09B 19/0092 434/127 |
| 10,978,176 B2* | 4/2021 | Cha ...................... | G16H 50/20 |
| 2005/0182659 A1* | 8/2005 | Huttin ................... | G06Q 10/10 705/2 |
| 2014/0074510 A1* | 3/2014 | McClung .............. | G16H 50/30 705/3 |
| 2018/0082038 A1* | 3/2018 | Blair, II ................ | G16H 10/65 |
| 2019/0286656 A1* | 9/2019 | Yerva .................... | G06N 3/044 |
| 2019/0295440 A1* | 9/2019 | Hadad .................. | G06F 40/295 |
| 2020/0005900 A1* | 1/2020 | Cha ....................... | G16B 50/00 |
| 2020/0065681 A1* | 2/2020 | Wolf ..................... | G16H 10/40 |
| 2020/0152312 A1* | 5/2020 | Connor ................. | G06V 20/20 |
| 2020/0261009 A1* | 8/2020 | Everman .............. | G16H 40/40 |

FOREIGN PATENT DOCUMENTS

WO WO-2016050958 A1 * 4/2016 ......... G06F 19/3475

* cited by examiner

*Primary Examiner* — Robert W Morgan
*Assistant Examiner* — Edward B Winston, III
(74) *Attorney, Agent, or Firm* — Caldwell Intellectual Property Law

(57) ABSTRACT

A system for calculating an edible score in a display interface, including a computing device configured to initiate, a display interface; retrieve, a performance profile relating to a user; determine, an edible of interest; receive, nourishment information relating to the edible of interest; generate, a score machine-learning process to output an edible score; and display, the edible score within the display interface.

18 Claims, 11 Drawing Sheets

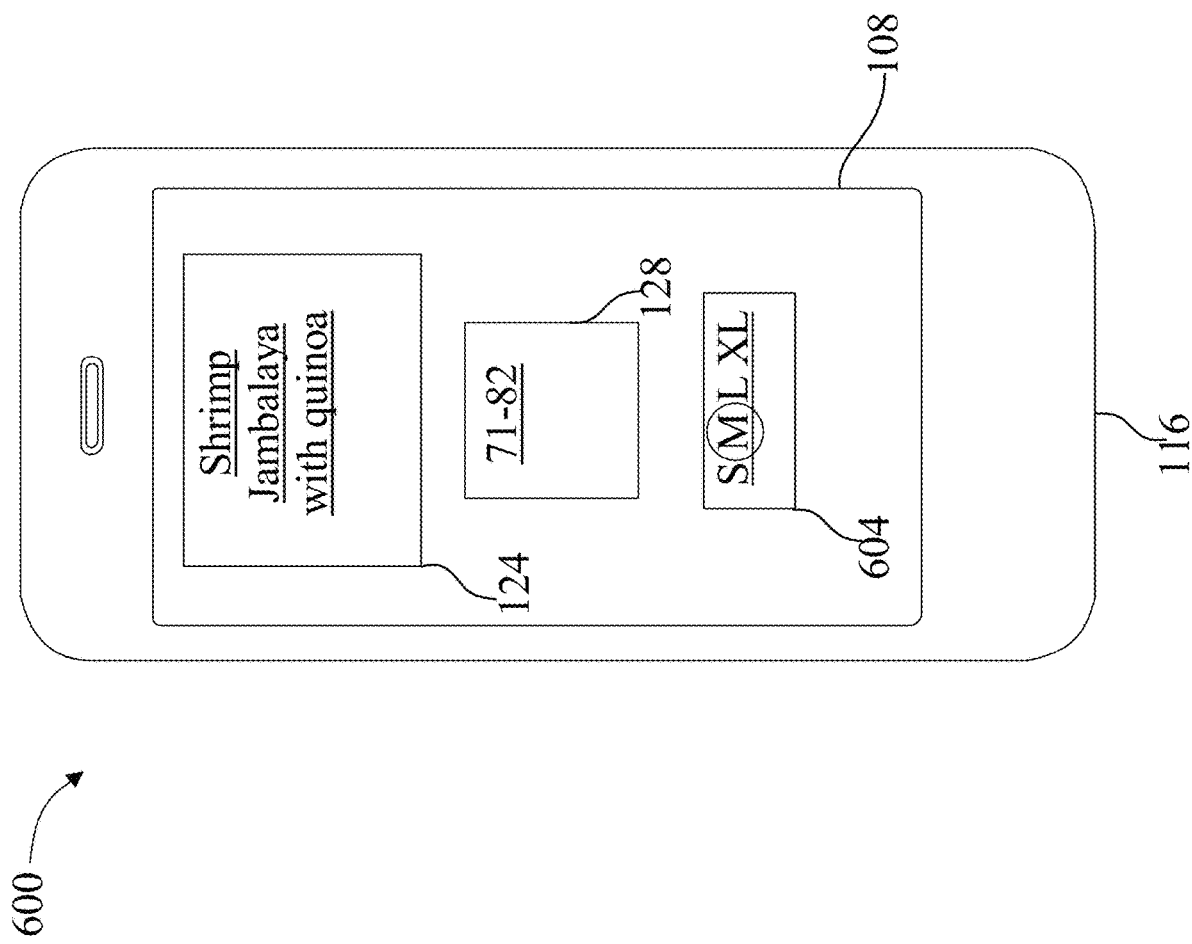

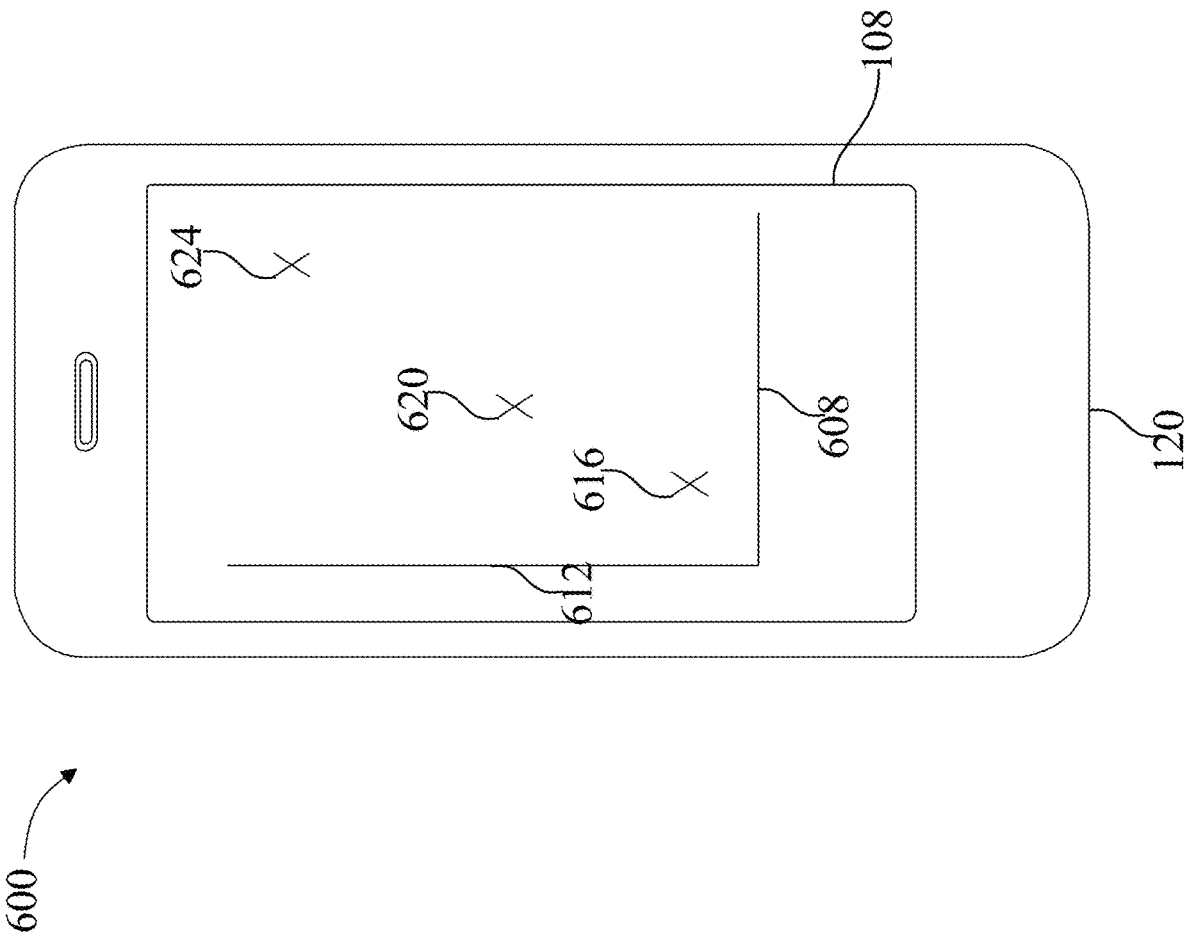

METHODS AND SYSTEMS FOR CALCULATING AN EDIBLE SCORE IN A DISPLAY INTERFACE

CROSS-REFERENCE TO RELATED APPLICATIONS

This application is a continuation-in-part of Non-provisional application Ser. No. 16/983,034 filed on Aug. 3, 2020 and entitled "METHODS AND SYSTEMS FOR CALCULATING AN EDIBLE SCORE IN A DISPLAY INTERFACE," the entirety of which is incorporated herein by reference.

FIELD OF THE INVENTION

The present invention generally relates to the field of nourishment. In particular, the present invention is directed to methods and systems for calculating an edible score in a display interface.

BACKGROUND

Understanding how much to eat, and what types of foods to eat can be challenging. Frequently, users are overloaded with conflicting information. A void exists to deliver custom food suggestions that indicate how a particular food will uniquely affect a consumer.

SUMMARY OF THE DISCLOSURE

In an aspect, a system for calculating a score for an edible in a display interface includes a computing device configured to determine an edible of interest, receive nourishment information relating to the edible of interest to a user, generate a score machine-learning process, wherein generating the score machine-learning process includes training the score machine-learning process using edible training data, wherein edible training data contains a plurality of data entries, each data entry containing a performance profile and nourishment information and a correlated score data and calculating the score as a function of the score machine-learning process, wherein the score machine-learning process uses the performance profile and the nourishment information relating to the edible of interest as an input, and outputs the score, determine a cost associated with the edible, calculate a cost to score ratio as a function of the cost and the score, and display the cost to score ratio within a display interface.

In another aspect, a method of calculating a score for an edible in a display interface includes determining an edible of interest. The method includes receiving nourishment information relating to the edible of interest to a user. The method includes generating a score machine-learning process, wherein generating the score machine-learning process further includes training the score machine-learning process using edible training data, wherein edible training data contains a plurality of data entries, each data entry containing a performance profile and nourishment information and a correlated score data and calculating the score as a function of the score machine-learning process, wherein the score machine-learning process uses the performance profile and the nourishment information relating to the edible of interest as an input, and outputs the score. The method includes determining a cost associated with the edible. The method includes calculating a cost to score ratio as a function of the cost and the score. The method includes displaying the cost to score ratio within a display interface.

In an aspect, a method of calculating an edible score in a display interface, the method comprising initiating by a computing device, a display interface; retrieving by the computing device, a performance profile relating to a user; determining by the computing device, an edible of interest; receiving by the computing device, nourishment information relating to the edible of interest; generating by the computing device, an score machine-learning process, wherein generating the score machine-learning process further comprises training the score machine-learning process using edible training data, wherein edible training data contains a plurality of data entries containing a performance profile and nourishment information relating to a edible correlated to an edible score; and calculating the score machine-learning process as a function of training the score machine-learning process, wherein the score machine-learning process uses the performance profile and the nourishment information relating to the edible of interest as an input, and outputs the edible score; and displaying by the computing device, the edible score within the display interface.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 6A-6C are diagrammatic representations of display interface;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for calculating an edible score in a display interface. In an embodiment, a performance profile is used together with an edible of interest, and using a score machine-learning process, to calculate an edible score. An edible score is displayed within display interface, to aid a user in making informed food selections.

Figure 1:
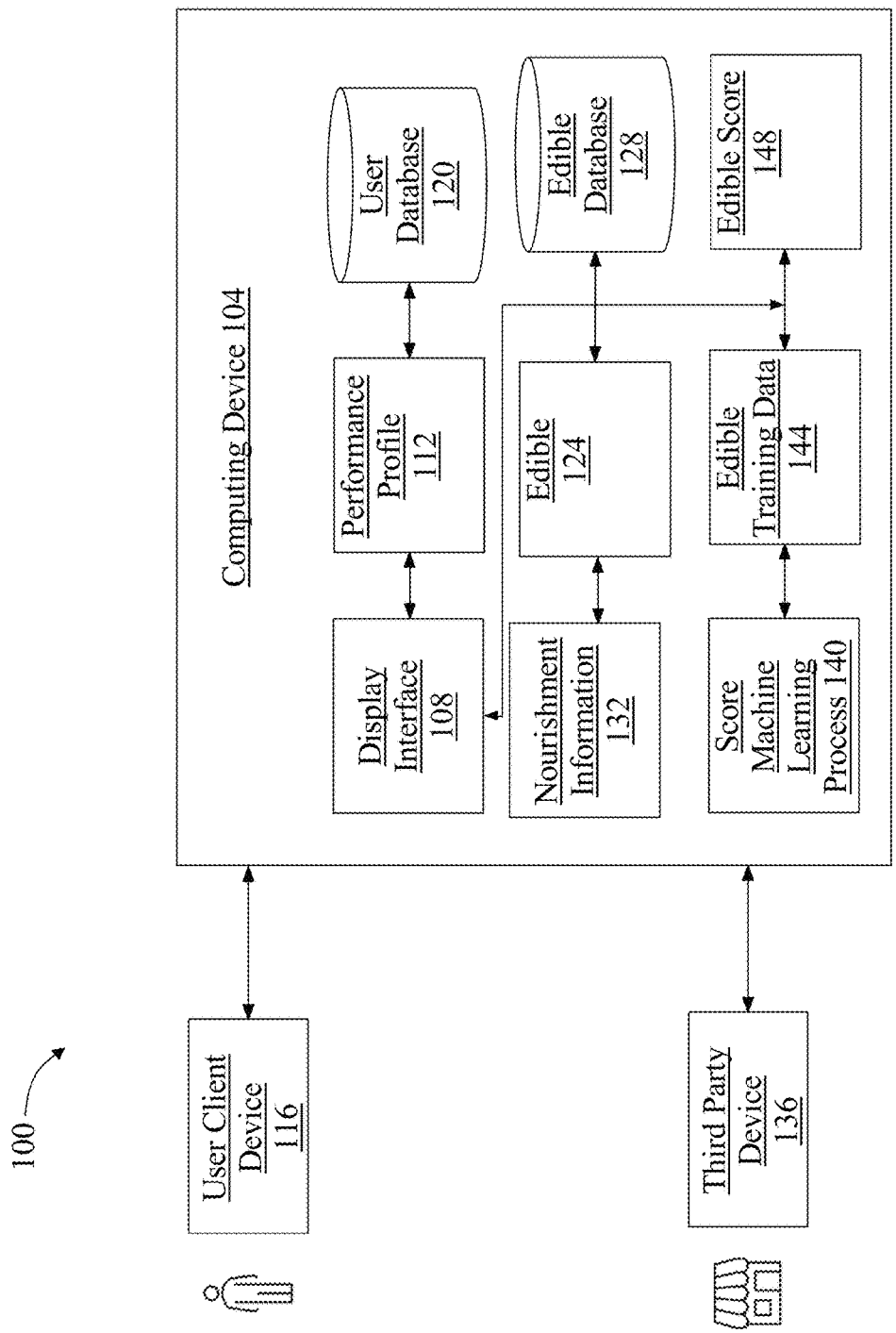
FIG. 1 is a block diagram illustrating an exemplary embodiment of a system for calculating an edible score in a display interface.

Referring now to the drawings, FIG. 1 illustrates an exemplary embodiment 100 of a system for calculating an edible score in a display interface. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or connect with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or connect with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an association, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be transmitted to and/or from a computer and/or a computing device 104. Computing device 104 may include but is not limited to, for example, a computing device 104 or cluster of computing devices 104 in a first position and a second computing device 104 or cluster of computing devices 104 in a second position. Computing device 104 may include one or more computing devices 104 dedicated to data storage, security, dispersal of traffic for load balancing, and the like. Computing device 104 may distribute one or more computing tasks as described below across a plurality of computing devices 104 of computing device 104, which may operate in parallel, in series, redundantly, or in any other manner used for dispersal of tasks or memory between computing devices 104. Computing device 104 may be implemented using a "shared nothing" architecture in which data is cached at the operative, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence recurrently until a desired or commanded outcome is achieved; repetition of a step or a sequence of steps may be performed iteratively and/or recursively using outputs of previous repetitions as inputs to subsequent repetitions, assembling inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to initiate a display interface within computing device 104. A "display interface," as used in this disclosure, is a user interface that allows a user to interface with computing device 104 through graphical icons, audio indicators, command labels, text navigation and the like. Display interface 108 may include a form or other graphical element having display fields, where one or more elements of information may be displayed. Display interface 108 may include slides or other user commands that may allow a user to select one or more characters. Display interface 108 may include free form textual entries, where a user may type in responses and/or messages. Display interface 108 may display data output fields including text, images, or the like. Display interface 108 may include data input fields such as text entry windows, drop-down lists, buttons, checkboxes, radio buttons, sliders, links, or any other data input interface that may capture user interaction as may occur to persons skilled in the art upon reviewing the entirety of this disclosure. Display interface 108 may be provided, without limitation, using a web browser, a native application, a mobile application, or the like.

With continued reference to FIG. 1, computing device 104 is configured to retrieve, a performance profile 112 relating to a user. A "performance profile," as used in this disclosure, is a compilation of one or more elements of data, relating to one or more aspects of a user's body, lifestyle, beliefs, and/or practices. An element of data may include biological extraction data. A "biological extraction," as used in this disclosure, is any data indicative of a person's physiological state; physiological state physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. A biological extraction includes without limitation any biological extraction as described in U.S. Nonprovisional application Ser. No. 16/530,329 filed on Aug. 2, 2019 and entitled "METHODS AND SYSTEMS FOR GENERATING COMPATIBLE SUBSTANCE INSTRUCTION SETS USING ARTIFICIAL INTELLIGENCE," the entirety of which is incorporated herein by reference. An element of data may include any information relating to current levels of age related degradation. Age related degradation may include any physiological changes that occur within the human body. For example, age related degradation may include thinning and loss of elasticity of the skin. In yet another non-limiting example, age related degradation may include a decrease in the production of natural oils, which may cause the skin to become drier. An element of data may include information relating to a user's sleep patterns, including information describing quantities of sleep, quality of sleep, information pertaining to sleep cycles, nighttime wakefulness, daytime drowsiness, daytime sleeping patterns, and the like. For example, an element of data may specify that a user sleeps on average over the previous one week, a total of 7 hours each night. An element of data may include information relating to a user's fitness patterns such as how much exercise a user engages in, types of exercise that a user engages in, frequency of exercise, exercise groups that a user is a member of, exercise classes that a user partakes in, and the like. For example, an element of data may specify that over the previous week, a user exercised a total of one hundred twenty minutes, of which forty minutes were spent on weight bearing exercise, and eighty minutes were spent on cardiovascular exercise that included a mix of walking and running. An element of data may include information relating to a user's nutritional status, such as any information describing any self-reported food allergies, food sensitivities, dietary requests, style of eating, and the like that the user may be following. For example, an element of data may specify that a user follows a vegan diet for ethical and personal religious reasons. A performance profile may include any information suitable for use as a nourishment score, as described in U.S. Nonprovisional application Ser. 16/886,673 filed on May, 22, 2020, and entitled "METHODS AND SYSTEMS FOR GEOGRAPHICALLY TRACKING NOURISHMENT SELECTION," the entirety of which is incorporated herein by reference.

With continued reference to FIG. 1, an element of data may include information relating to a user's stress levels, such as information describing how often a user feels stressed in an average week, how much stress on average a user feels over a specified period of time, triggers of stress for the user, stress coping mechanisms, and the like. For example, an element of data may specify that a user feels extremely stressed out before presentations, but that deep breathing exercises help mitigate feelings of stress for the user. In yet another non-limiting example, an element of data may specify that a user feels most stressed out at the beginning of the week when the user has a lot of items to complete, and the user feels less stressed out as the week progresses, and the user starts to complete certain items. An element of data may include information relating to a user's toxicity level. A toxicity level, may include any information describing a degree to which a substance and/or any mixture of one or more substances has damaged a user's body. A toxicity level may contain one or more indicators of substances that include, but are not limited to heavy metals, solvents, volatile organic compounds, pesticides, bisphenol A, phthalates, parabens, electromagnetic field radiation, heterocyclic amines, intestinal bacteria, yeast, candida, infectious disease, food additives, chemicals, glyphosate, insulin resistance, medications, stress, and/or emotions. For example, a toxicity level may include one or more measurements of heavy metals such as aluminum, antimony, arsenic, barium, beryllium, bismuth, cadmium, cesium, gadolinium, lead, mercury, nickel, palladium, platinum, tellurium, thallium, thorium, tin, tungsten, uranium, and the like. An element of data may include information relating to a user's emotional and/or psychological state, including one or more indicators of age, sex, financial well-being, sedentary lifestyle, career stress, personal relationships, significant life events such as a death in the family or a divorce, unresolved emotional trauma, post-traumatic stress disorder, and the like.

With continued reference to FIG. 1, a performance profile 112 may be obtained utilizing a questionnaire. A "questionnaire," as used in this disclosure, is an instrument containing one or more prompts for information from a participant such as a user. A questionnaire may include one or more questions prompting a user to respond to a request to obtain information relating to a performance profile 112. In an embodiment, computing device 104 may display a questionnaire within display interface 108. A questionnaire may include one or more question styles and/or types of questions including but not limited to true or false questions, multiple choice questions, ordering questions, open ended essay questions, fill in the blank questions, matching questions, and the like. For example, a questionnaire may include a question asking a user to describe the user's sleeping habits over the course of the previous night. One or more answers to a questionnaire may be obtained from a user client device 116, operated by a user. A user client device 116 may include without limitation, an additional computing device such as a mobile device, laptop, desktop computer, and the like. A user client device 116 may include, without limitation, a display in communication with computing device 104.

With continued reference to FIG. 1, a performance profile 112 may be obtained from sensor data. Sensor data may be obtained from any sensor and/or medical device configured to capture sensor data concerning a user, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmography equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. A wearable and/or mobile device sensor may capture step, gait, and/or other mobility data, as well as data describing activity levels and/or physical fitness. A wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, information relating to a performance profile 112 may be stored within user database 120. User database 120 may be implemented, without limitation, as a relational database, a key-value retrieval datastore such as a NOSQL database, or any other format or structure for use as a datastore that a person skilled in the art would recognize as suitable upon review of the entirety of this disclosure.

With continued reference to FIG. 1, computing device 104 is configured to determine, an edible of interest. An "edible," as used in this disclosure, is any substance consumed by a human being. An edible 124 may include a single ingredient, a combination of one or more ingredients, a meal including breakfast, lunch, dinner, snack, dessert, beverage, and/or any combination thereof. For instance and without limitation, an edible 124 may include a breakfast option such as buckwheat pancakes topped with fresh berries and raw honey. In yet another non-limiting example, an edible 124 may include a beverage such as ginger lime kombucha. An "edible of interest," as used in this disclosure, is any edible 124 that computing device 104 selects to present to a user within display interface 108, as a possible item that a user may be interested in and/or may wish to consume. An edible of interest may be identified based on information contained within user database 120, including information relating to a user's dietary habits. A "dietary habit," as used in this disclosure, is data including any character, numerical, and/or symbolic data representing a user's eating patterns. A dietary habit may include information relating to a user's food preferences, style of eating, food likes, food dislikes, mealtimes, average number of meals consumed each day, and the like. For instance and without limitation, a dietary habit may specify that a user consumes two meals per day, with a first meal generally around 1 PM, and a second meal around 6 PM. In yet another non-limiting example, a dietary habit may specify that a user follows a vegan diet for breakfast and lunch but consumes seafood at dinner. In yet another non-limiting example, a dietary habit may specify that a user dislikes asparagus, and the user abstains from eating asparagus. Information relating to a use's dietary habits may be stored within user database 120.

With continued reference to FIG. 1, computing device 104 may identify an edible of interest using information relating to a user's geolocation. A "geolocation," as used in this disclosure, is a real-world geographical location of a user. A geolocation may include a global positioning system (GPS) of a user, and/or geographic coordinates that specify the latitude and longitude of particular location where a user is located. A geolocation may be obtained from a radar source, user client device 116, self-reported by the user, and the like. Computing device 104 receives an element of user geolocation data and identifies a plurality of edibles as a function of the element of user geolocation data. Information pertaining to an edible 124 may be stored within edible database 128. Edible database 128 may be implemented as any data structure suitable for use as user database 120, as described above in more detail. In an embodiment, computing device 104 may generate a query, to search for edibles 124 that may be available within the user's geolocation. A "query," as used in this disclosure, is any search term used to retrieve information relating to an edible 124, from a database, such as edible database 128. For instance and without limitation, computing device 104 may utilize a user's geolocation that specifies a user is located in Anchorage, Alaska to generate a query containing "Anchorage, Alaska." to identify a plurality of edibles 124 available within Anchorage, Alaska. Computing device 104 displays a plurality of edibles 124 within display interface 108 and receives a user selection containing an edible of interest. A user selection may include any user choice, picking one or more edibles 124 from within a plurality of edibles 124. A user selection may be received from user client device 116.

With continued reference to FIG. 1, computing device 104 receives, nourishment information relating to an edible of interest. "Nourishment information," as used in this disclosure, is data, including any numerical, character, and/or symbolic data, describing the nutritional content of an edible 124. Nourishment information 132, may include information describing the contents and/or ingredients of an edible and/or the impact of an edible 124 on a human body. Nourishment information 132 may include a caloric input, describing the total calorie count contained within an edible 124. Nourishment information 132 may include a nutrient input, describing the total quantities of one or more nutrients contained within an edible 124. For example, a nutrient input may describe the total number of carbohydrates, fats, proteins, minerals, additives, enzymes, vitamins, sugar, cholesterol, and the like contained within a specified serving of an edible 124. For instance and without limitation, nourishment information 132 may specify that an edible containing a dinner option containing chicken parmesan with baked ziti contains 1200 calories in a serving size that equates to half of the dinner option. In yet another non-limiting example, nourishment information 132 may specify that a salad containing tuna fish and avocado in a green goddess dressing contains 400 calories in the entire salad, and contains 16 grams of fat, 20 grams of protein, 10 grams of carbohydrates, 6 grams of sugar, and 6 grams of fiber. Nourishment information 132 may be obtained from third party device 136 and stored within edible database 128. Third party device 136, may include any device suitable for use as user client device 116, as described above in more detail. An entry containing nourishment information 132 may be generated by a meal maker who prepares and/or cooks an edible 124, one or more experts in the field of nutrition and nourishment such as scientists, dieticians, nutritionists, researchers, clinicians, medical professionals and the like. Information relating to nourishment information 132 may be updated in real time, using any network methodology as described herein. Information pertaining to nourishment information 132 may be stored within edible database 128.

With continued reference to FIG. 1, computing device 104 may determine nourishment information 132, using a dietary classifier. A "classifier," as used in this disclosure, is a process in which computing device 104 sorts inputs into categories or bins of data. A classifier may be generated using a classification process, including a classification algorithm. Classification may be performed using any of the classification processes and/or classification algorithms as described in U.S. Nonprovisional application Ser. No. 16/699,616 filed on Nov. 30, 2019, and entitled "METHODS AND SYSTEMS FOR INFORMING FOOD ELEMENT DECISIONS IN THE ACQUISITION OF EDIBLE MATERIALS FROM ANY SOURCE," the entirety of which is incorporated herein by reference. A "dietary classifier," as used in this disclosure, is a classifier that uses an edible of interest as an input and outputs, a dietary label using a classification process. A "dietary label," as used in this disclosure, identifies one or more dietary patterns and/or ways of eating that an edible 124 may fulfill. For example, a dietary label may indicate that an edible 124 containing quinoa linguine cooked with olive oil, basil and tomatoes and topped with shrimp fulfills a Mediterranean diet, a gluten free diet, a dairy free diet, a pescatarian diet, and the like. Dietary classifier may be trained using training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data may be obtained from expert inputs, previous iterations of generating a classification process, and the like.

With continued reference to FIG. 1, computing device 104 is configured generate a score machine-learning process. A "machine-learning process," as used in this disclosure, is a process that automatedly uses training data to generate a model and/or an algorithm, that will be performed by computing device 104, to produce outputs given data provided as inputs; this is in contrast to a non-machine learning software program where the commands to be executed are determined in advance by a user and written in a programming language. An "score machine-learning process," as used in this disclosure, uses a performance profile 112 and nourishment information 132 relating to an edible of interest as an input, and outputs an edible score. Generating a score machine-learning process 132 includes training score machine-learning process 132 using edible training data 144. "Edible training data," as used in this disclosure, is training data containing a plurality of data entries containing a performance profile and nourishment information relating to an edible 124, correlated to an edible score. Edible training data 144 may be obtained from expert inputs and/or previous iterations of generating score machine-learning process 140. Score machine-learning process 140 may be implemented as any machine learning process as described in U.S. Nonprovisional application Ser. 16/372,512 filed on Apr. 2, 2019 and entitled "METHODS AND SYSTEMS FOR UTILIZING DIAGNOSTICS FOR INFORMED VIBRANT CONSTITUTIONAL GUIDANCE," the entirety of which is incorporated herein by reference.

With continued reference to FIG. 1, score machine-learning process 140 outputs an edible score 148. An "edible score," as used in this disclosure, is data, including any character, symbolic, and/or numerical data, containing a score reflecting the nutritional impact of an edible on a user's body and/or health. An edible score 148 may be transient and/or dynamic. An edible score 148 may be graded on a continuum, where a score of zero may indicate an edible that will have an extremely poor nutritional impact on a user, while a score of 100 may indicate an edible that will have an excellent nutritional impact on a user. An edible score may be updated based on a serving size of an edible.

With continued reference to FIG. 1, computing device 104 may be configured to calculate a first edible score 148 for a first edible 124, calculate a second edible score 148 for a second edible 124, and chart the first edible score 148 as a function of the second edible score 148. Charting may include mapping and/or graphing a first edible score 148 as compared to a second edible score 148. For instance and without limitation, a first edible 124 that contains a first edible score 148 of 74 for a first edible 124 containing grilled salmon served with rice pilaf and steamed broccoli may be charted on a graph versus a second edible 124 that contains a second edible score 148 of 22 for a second edible 124 containing fried chicken served with mashed potatoes and gravy. A chart may be displayed within display interface 108 for a user to view a first edible score charted as a function of a second edible score.

Figure 2:
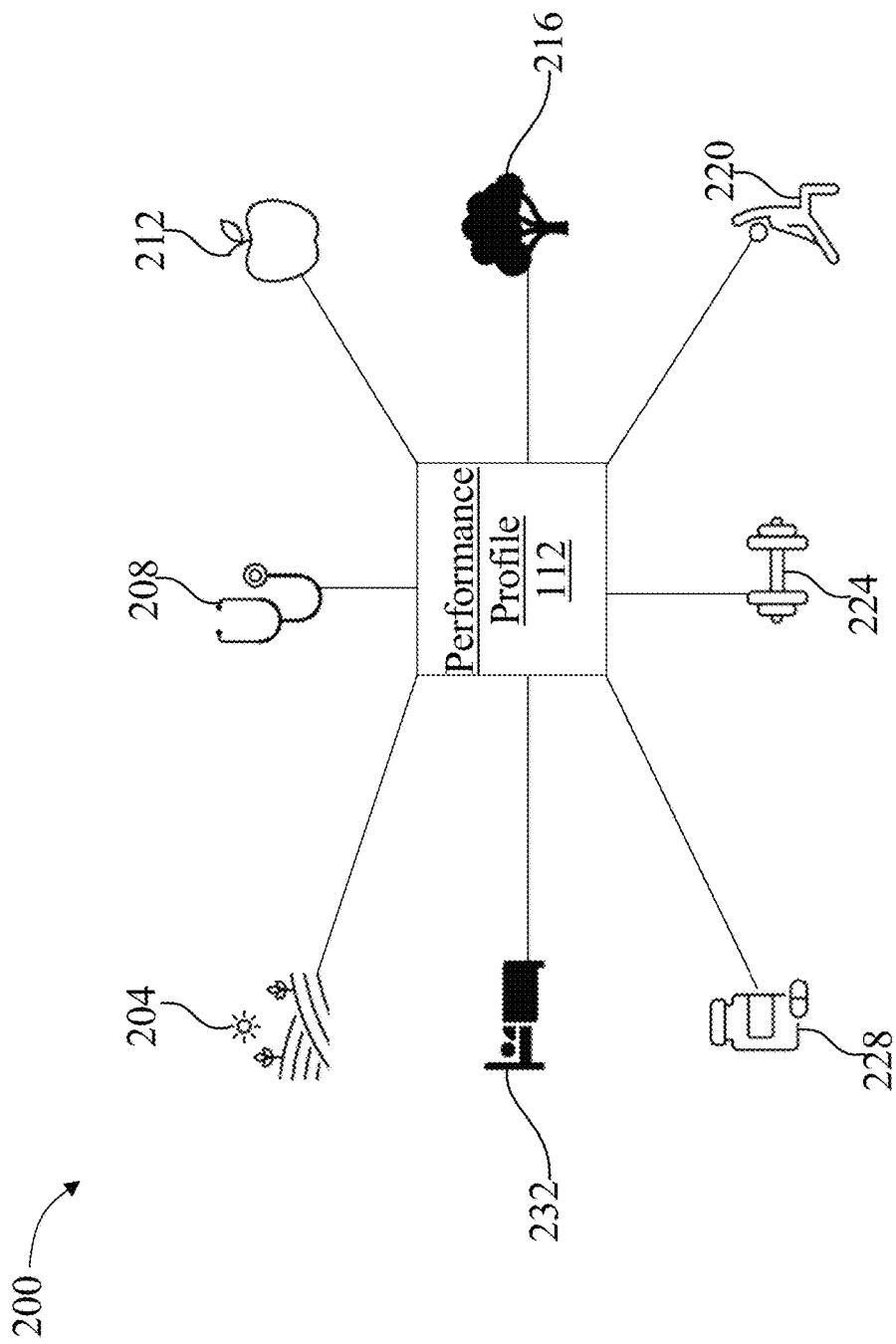
FIG. 2 is a diagrammatic representation of a performance profile.

Referring now to FIG. 2, an exemplary embodiment 200 of performance profile 112 is illustrated. Performance profile 112 may include one or more elements of data relating to a user, as described above in more detail in reference to FIG. 1. A performance profile 112, may include an element of data 204 relating to a user's access to nature and fresh air and/or how many hours a day a user spending indoors under artificial lights. For example, a performance profile 112 may indicate that a user spends on average thirty minutes outdoors every morning before heading to work. A performance profile 112, may include an element of data 208 relating to a user's access to medical care and medical services. For example, a performance profile 112 may contain a biological extraction from a user, such as findings from a CAT (CT) scan, showing a complex bone fracture. A performance profile 112, may include an element of data 212 relating to a user's current eating habits. For example, a performance profile 112 may contain an indication that a user dislikes all pork containing products, and the user likes all poultry containing products. A performance profile 112 may include an element of data 216 relating to a user's toxicity levels, including any of the toxicity levels as described above in more detail in reference to FIG. 1. For example, a performance profile 112 may contain an indication that a user has high urinary levels of cadmium. A performance profile 112, may include an element of data 220 relating to a user's stress levels, meditation practice, and/or overall body flexibility. For example, a performance profile 112 may contain an indication that a user practices hatha yoga three days each week. A performance profile 112 may include an element of data 224 relating to a user's fitness and/or activity level. For example, a performance profile 112 may contain an indication that a user engages in three days of biking each week, and two days of strength training each week. A performance profile 112 may include an element of data 228 relating to a user's medication and/or supplement use. For example, a performance profile 112 may contain an indication that a user takes a prescription medication for osteoporosis, and an iron containing supplement. A performance profile 112 may include an element of data 232 relating to a user's sleeping patterns and sleeping habits. For example, a performance profile 112 may contain an indication that over the past week the user has slept an average of six and a half hours each night and taken an average of twenty two minutes to fall asleep each night.

Figure 3:
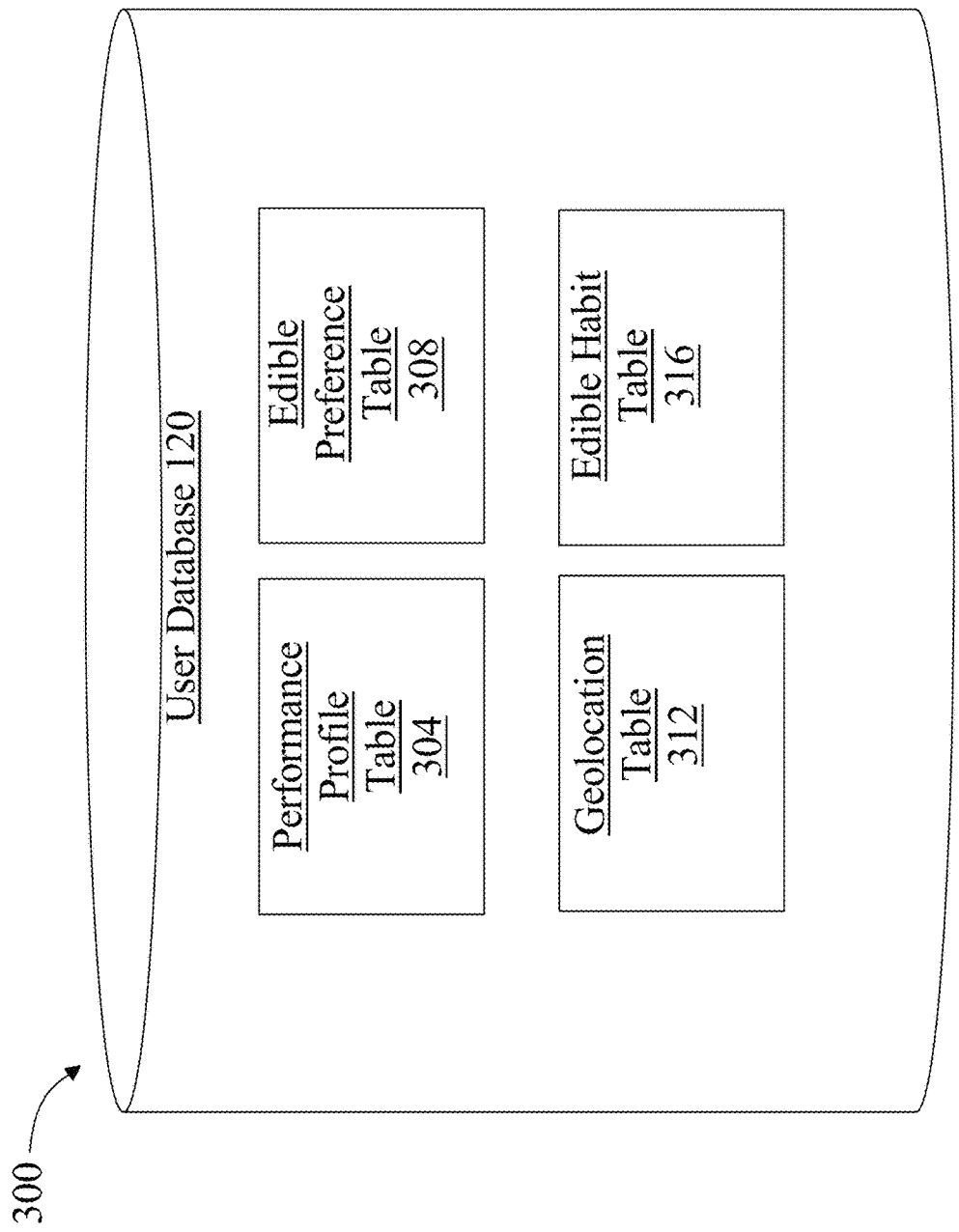
FIG. 3 is a block diagram illustrating an exemplary embodiment of a user database.

Referring now to FIG. 3, an exemplary embodiment 300 of user database 120 is illustrated. User database 120 may be implemented as any data structure suitable for use as described above in more detail in reference to FIG. 1. One or more tables contained within user database 120 may include performance profile table 304; performance profile table 304 may include any information relating to a user's performance profile 112. For instance and without limitation, performance profile table 304 may include information describing a user's sleeping patterns over the prior week, including information specifying how much sleep a user got each night, as well as how many rapid eye movement (REM) cycles a user entered. One or more tables contained within user database 120 may include edible preference table 308; edible preference table 308 may include information describing a user's food preferences. For instance and without limitation, edible preference table 308 may indicate that a user likes foods that are spicy, but the user does not like meals that contain cucumbers. One or more tables contained within user database 120 may include geolocation table 312; geolocation table 312 may include any indication as to a user's geolocation. For instance and without limitation, geolocation table 312 may specify that a user is currently located in Bangor, Maine One or more tables contained within user database 120 may include edible habit table 316; edible habit table 316 may include information describing a user's edible habits. For instance and without limitation, edible habit table 316 may specify that a user skips breakfast every morning, but eats lunch and dinner, and one afternoon snack.

Figure 4:
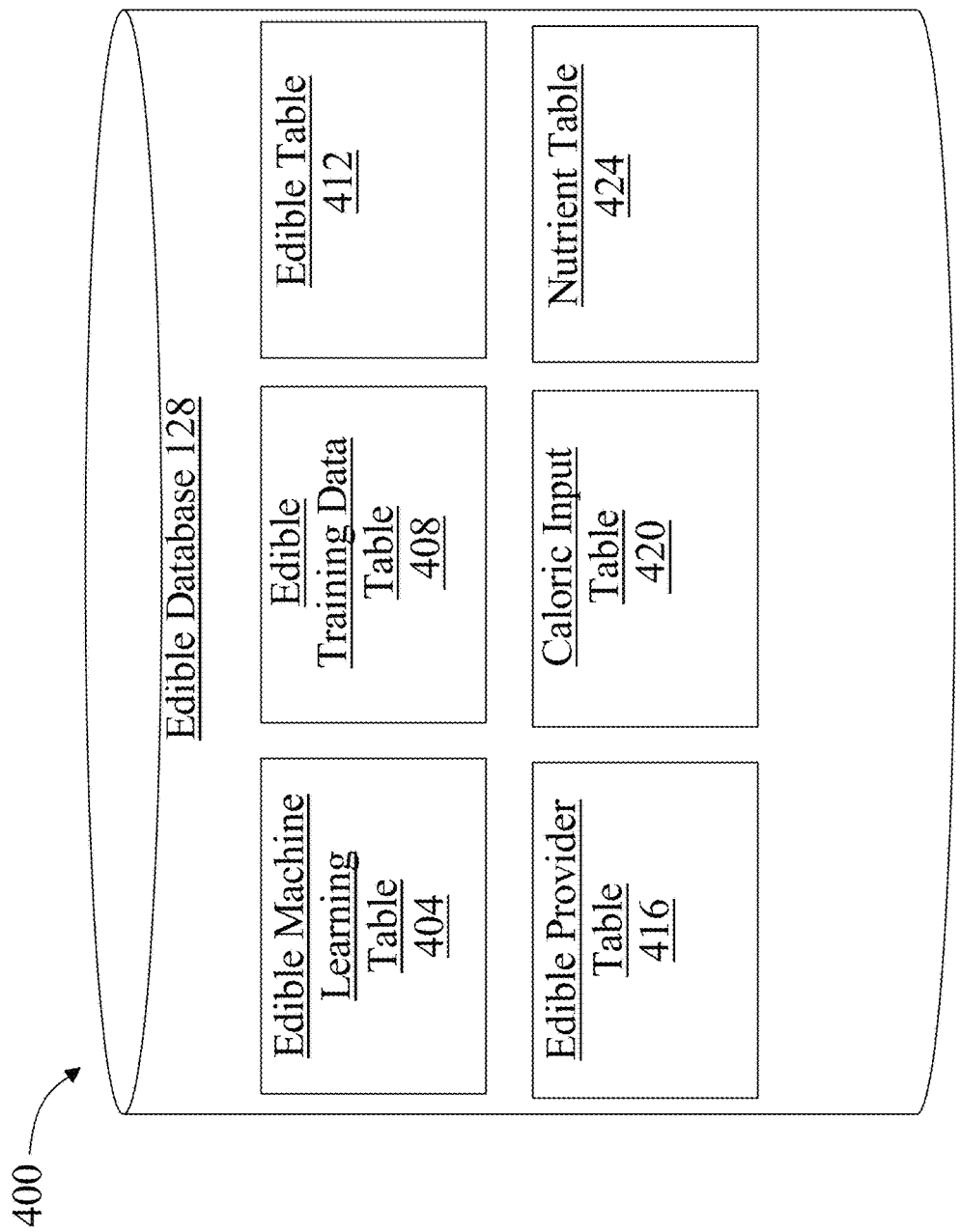
FIG. 4 is a block diagram illustrating an exemplary embodiment of an edible database.

Referring now to FIG. 4, an exemplary embodiment 400 of edible database 128 is illustrated. Edible database 128 may be implemented as any data structure as described above in more detail in reference to FIG. 1. One or more tables contained within edible database 128 may include score machine-learning table 404; score machine-learning table 404 may include information relating to score machine-learning process 140. One or more tables contained within edible database 128 may include edible training data table 408; edible training data table 408 may include information relating to one or more edible training data sets 144. One or more tables contained within edible database 128 may include edible table 412; edible table 412 may include information relating to one or more edibles 124. One or more tables contained within edible database 128 may include edible provider table 416; edible provider table 416 may include information relating to one or more edible providers, such as a meal maker. One or more tables contained within edible database 128 may include caloric input table 420; caloric input table 420 may include information relating to the caloric input of one or more edibles 124. One or more tables contained within edible database 128 may include nutrient table 424; nutrient table 424 may include information relating to the nutrient input of one or more edibles 124.

Figure 5:
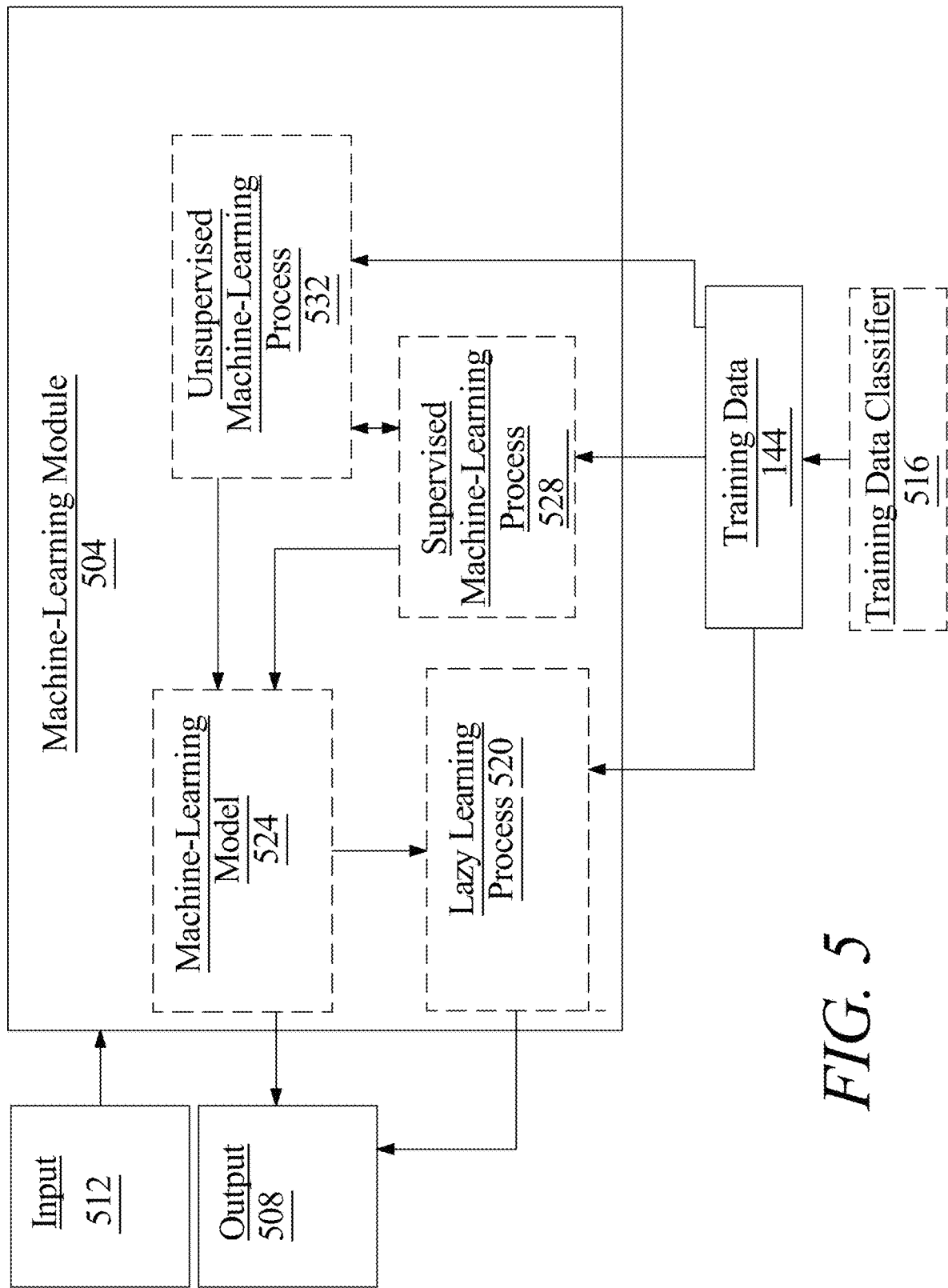
FIG. 5 is a block diagram illustrating an exemplary embodiment of a machine-learning module.

Referring now to FIG. 5, an exemplary embodiment 500 of a machine-learning module 504 that may perform one or more machine-learning processes as described in this disclosure, is illustrated. Machine-learning module may perform determinations, classification, and/or analysis steps, methods, processes, or the like as described in this disclosure using machine learning processes, including for example, score machine-learning process 140. A machine learning process includes any of the machine-learning processes as described above in more detail in reference to FIG. 1. Machine learning module 504 uses edible training data 144 to generate an algorithm that will be performed by computing device 104 and/or machine-learning module 504 to produce outputs 508 such as edible score 148 given data provided as inputs 512, such as performance profile 112 and/or edible 124.

With continued reference to FIG. 5, edible training data 144 may include any of the edible training data 144 as described above in more detail in reference to FIG. 1. Multiple data entries in training data 144 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 144 according to various correlations; correlations may indicate causative and/or predictive links between categories of data elements, which may be modeled as relationships such as mathematical relationships by machine-learning processes as described in further detail below. Training data 144 may be formatted and/or organized by categories of data elements, for instance by associating data elements with one or more descriptors corresponding to categories of data elements. As a non-limiting example, training data 144 may include data entered in standardized forms by persons or processes, such that entry of a given data element in a given field in a form may be mapped to one or more descriptors of categories. Elements in training data 144 may be linked to descriptors of categories by tags, tokens, or other data elements; for instance, and without limitation, training data 144 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 144 may include one or more elements that are not categorized; that is, training data 144 may not be formatted or contain descriptors for some elements of data. Machine-learning algorithms and/or other processes may sort training data 144 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 144 to be made applicable for two or more distinct machine-learning algorithms as described in further detail below. Training data 144 used by machine-learning module 504 may correlate any input data as described in this disclosure to any output data as described in this disclosure. As a non-limiting illustrative example machine-learning module 504 may utilize performance profile 112 and/or edible 124 as an input and output an edible score 148.

Further referring to FIG. 5, edible training data 144 may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 504 may generate a classifier using a classification algorithm, defined as a processes whereby a computing device and/or any module and/or component operating thereon derives a classifier from edible training data 144. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to match certain elements of data contained within performance profile 112. For example, training data classifier 516 may characterize a sub-population such as a cohort of persons that contain user inputs that include sleeping patterns, or user inputs that contain toxicity levels. Training data classifier 516 may analyze items and/or phenomena contained within a performance profile 112 may be selected.

Still referring to FIG. 5, machine-learning module 504 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 144. Heuristic may include selecting some number of highest-ranking associations and/or training data 144 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate a machine-learning model. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 144 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include performance profile 112 and/or edible 124 as described above as inputs, edible score 148 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in edible training data 144. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 504 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 5, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from an edible training data 144 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using edible training data 144.

Figure 6B:
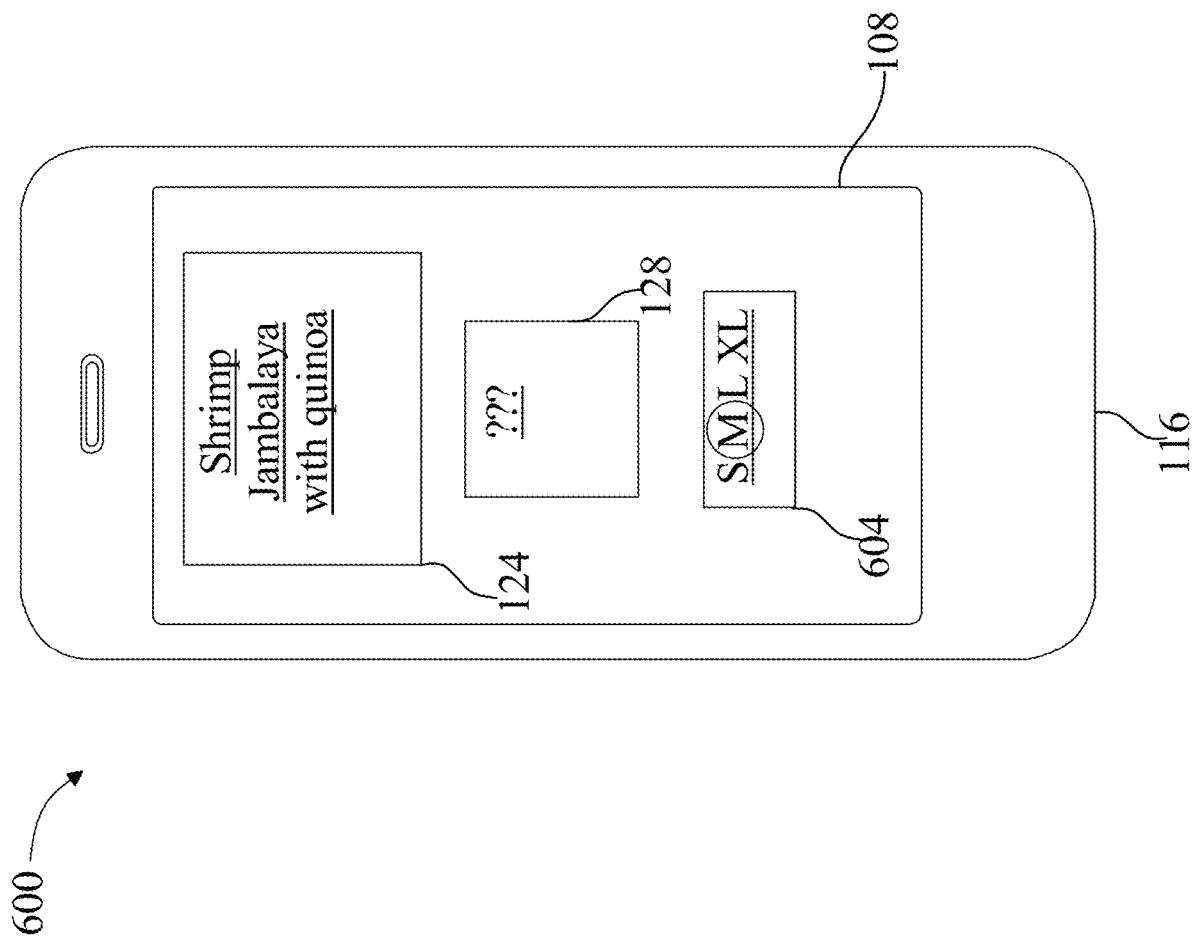

Referring now to FIGS. 6A-6C, exemplary embodiments 600 of display interface 108 are illustrated. Referring to FIG. 6A, in an embodiment, display interface 108 may be viewed by a user, on user client device 116. In an embodiment, display interface 108 may display a description of edible 124. Display interface 108 may display edible score 148 as a numerical output. In an embodiment, edible score 148 may be displayed based on a selected serving size 604 of edible 124. For example, a medium sized serving of shrimp jambalaya with quinoa may have an edible score 148 that ranges from 71-82, indicating that the edible 124, has a good nutritional impact on a user. Referring now to FIG. 6B, in an embodiment, edible score 148 may be displayed as "???" such as when edible score 148 may be unable to be calculated, such as when performance profile 112 does not contain enough information to calculate an edible score 148, or when an edible 124 may no longer be available or is out of stock. Referring now to FIG. 6C, display interface 108 may display a plurality of edibles charted as a function of an edible score for each of the plurality of edibles. A chart may include a graph, depicted in a diagrammatic form, containing an "X" axis 608, and a "Y" axis 612. In an embodiment, X axis 608 may contain each of a plurality of edibles 124, charted against a Y axis 612 containing each of a plurality of edible scores 148. In such an instance, display interface 108 may display a first edible 616 containing a first edible score, a second edible 620 containing a second edible score, and a third edible 624 containing a third edible score. In such an instance, third edible 624 may be displayed at almost the top of the Y axis 612, indicating it contains a very high edible score, as compared to first edible 616, which is displayed closer to the bottom of the Y axis 612, indicating it contains a much lower edible, while second edible 620 is located around the middle of Y axis 612, indicating it has a mediocre edible score. In such an instance, display interface 108 containing a chart of various edibles and corresponding edible scores may be utilized by a user to make an informed decision as to how each edible will impact a user's body.

Figure 7:
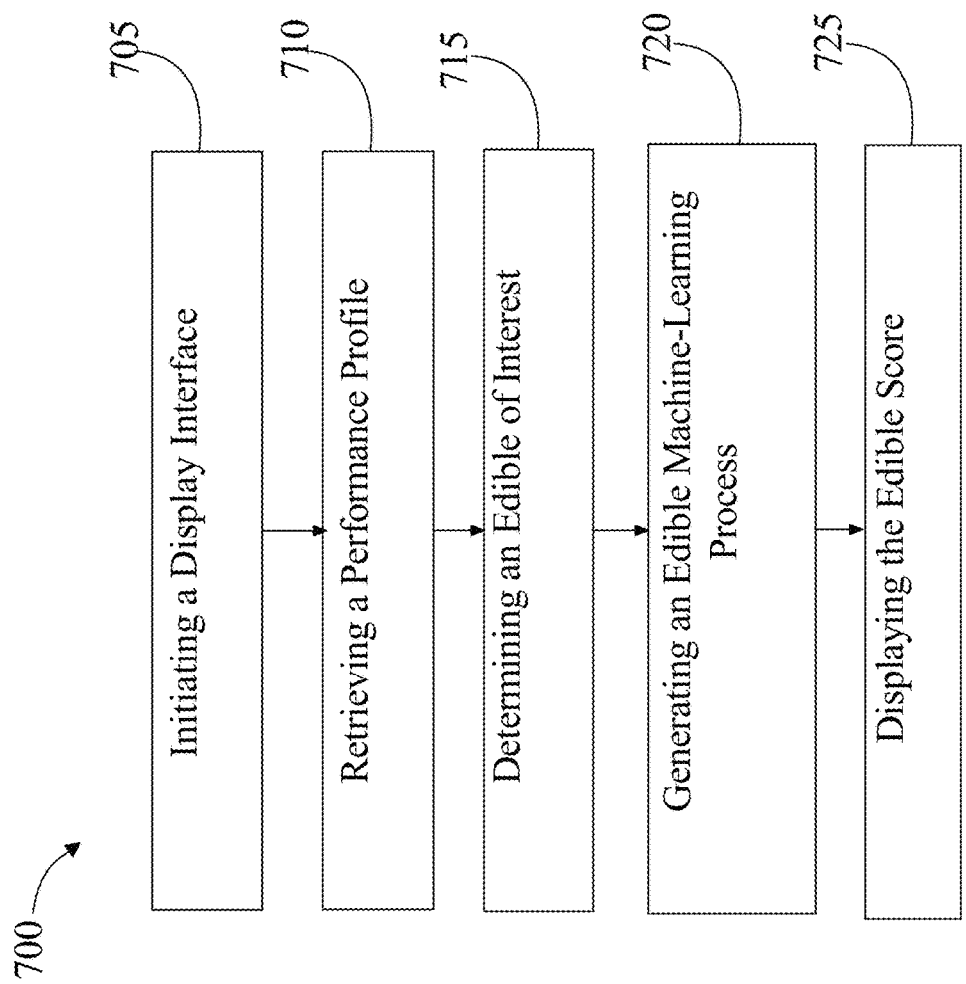
FIG. 7 is a process flow diagram illustrating an exemplary embodiment of a method of calculating an edible score in a display interface.

Referring now to FIG. 7, an exemplary embodiment 700 of a method of calculating an edible score in a display interface is illustrated. At step 705, computing device 104 initiates a display interface 108. Display interface 108 includes any of the display interfaces as described above in more detail in reference to FIG. 1. Display interface 108 may include a form or other graphical element having display fields, as described above in more detail.

With continued reference to FIG. 7, at step 710, computing device 104 retrieves a performance profile 112 relating to a user. A performance profile 112, includes any of the performance profiles 112 as described above in more detail in reference to FIG. 1. A performance profile 112 may include one or more elements of data relating to a user, as described above in more detail in reference to FIGS. 1-6. For instance and without limitation, a performance profile 112 may include a biological extraction relating to a user, such as a user's stool sample analyzed for one or more microorganism strains. In yet another non-limiting example, a performance profile 112 may include a user's toxicity levels, specifying that a user has high levels of cadmium in the user's blood. In yet another non-limiting example, a performance profile 112 may be obtained from sensor data, including any of the sensor data as described above in more detail in reference to FIG. 1. For example, a performance profile 112 may contain information about a user's heart rate while briskly walking, obtained from a sensor. Information relating to a performance profile 112 may be stored within user database 120. Information relating to a performance profile 112 may be obtained using a questionnaire as described above in more detail in reference to FIG. 1.

With continued reference to FIG. 7, at step 715, computing device 104 determines an edible 124 of interest. An edible 124 includes any of the edibles as described above in more detail in reference to FIG. 1. An edible 124 may include a meal option, such as a dinner option containing grilled salmon with asparagus and rice pilaf. In yet another non-limiting example, an edible may include a beverage option, such as an iced latte made with coconut milk. Computing device 104 determines an edible of interest, using a user's dietary habits. Information relating to edibles 124 and/or a user's dietary habits may be stored within edible database 128. For example, a user's dietary habits may indicate that a user likes red meat and chicken and dislikes all seafood. In such an instance, computing device 104 may identify an edible 124 of interest such as a lunch option that contains a bun less hamburger served with a side of sweet potato fries and a salad. One or more edibles 124 of interest, may be displayed to a user within display interface 108, whereby a user may select one or more edibles 124 of interest that look appealing to a user, and/or that a user may be interested in ordering from an edible provider, such as a meal maker.

With continued reference to FIG. 7, computing device 104 may determine an edible 124 of interest based on a user's geolocation. Computing device 104 receives an element of user geolocation data. Geolocation data includes any of the geolocation data as described above in more detail in reference to FIG. 1. Geolocation data may be obtained from a GPS located within user client device 116, and/or from a user input describing a user's location. Computing device 104 identifies a plurality of edibles as a function of the element of user geolocation data. For example, computing device 104 may generate a query to locate edibles available for purchase in Omaha, Nebraska, based on a user's geolocation in Omaha, Nebraska Computing device 104 displays a plurality of edibles 124 within display interface 108 and receives a user selection containing an edible 124 of interest.

With continued reference to FIG. 7, at step 720, computing device 104 receives nourishment information 132 relating to an edible 124 of interest. Nourishment information 132 includes any of the nourishment information 132 as described above in more detail in reference to FIG. 1. Nourishment information 132 may be stored within edible database 128 and may be received from third party device 136 operated by a third-party, such as an edible provider, meal-maker, scientist, nutritionist, dietician, medical professional, and the like. Nourishment information 132 may contain any of the nourishment information 132 as described above in more detail in reference to FIG. 1. Nourishment information 132 may contain a caloric input, such as a total number of calories contained within an edible 124. For example, nourishment information 132 may specify that a small serving of shrimp scampi over linguini has a total of 840 calories in the entire serving. Nourishment information 132 may contain a nutrient input, describing the total quantities of one or more nutrients contained within an edible 124. For example, a nutrient input for an edible containing a medium portion of vegan macaroni and cheese may specify that the vegan macaroni and cheese contains 14 grams of fat, 1 gram of saturated fat, 2 grams of polyunsaturated fat, 4 grams of monounsaturated fat, 200 milligrams of cholesterol, 50 grams of carbohydrates, 8 grams of fiber, and 14 grams of protein. Computing device 104 may determine nourishment information 132 by generating a dietary classifier, which may be implemented as any of the classifiers as described above in more detail in reference to FIG. 1. Dietary classifier uses an edible 124 of interest as an input, and outputs a dietary label using a classification process. Classification process includes any of the classification processes as described above in more detail in reference to FIG. 1.

With continued reference to FIG. 7, at step 725 computing device 104 generates a score machine-learning process 140. Score machine-learning process 140 may be implemented as any of the machine learning processes as described above in more detail in reference to FIGS. 1-5. Generating score machine-learning process 140 includes training score machine-learning process 140 using edible training data 144. Edible training data 144 may be implemented as any of the training data as described above in more detail in reference to FIG. 1. Edible training data 144 includes a plurality of data entries containing a performance profile and nourishment information relating to an edible correlated to an edible score. Generating score machine-learning process 140 includes calculating the score machine-learning process 140, where the score machine-learning process 140 uses a performance profile 112 and nourishment information 132 as an input, and outputs an edible score 148.

With continued reference to FIG. 7, at step 730, computing device 104 displays edible score 148 within display interface 108. Displaying edible score 148 includes calculating a first edible score 148 for a first edible 124 and calculating a second edible score 148 for a second edible 124. Computing device 104 charts first edible score 148 as a function of second edible score 148 and displays the chart within display interface 108. This may be performed for example, as described above in more detail in reference to FIG. 6.

Figure 8:
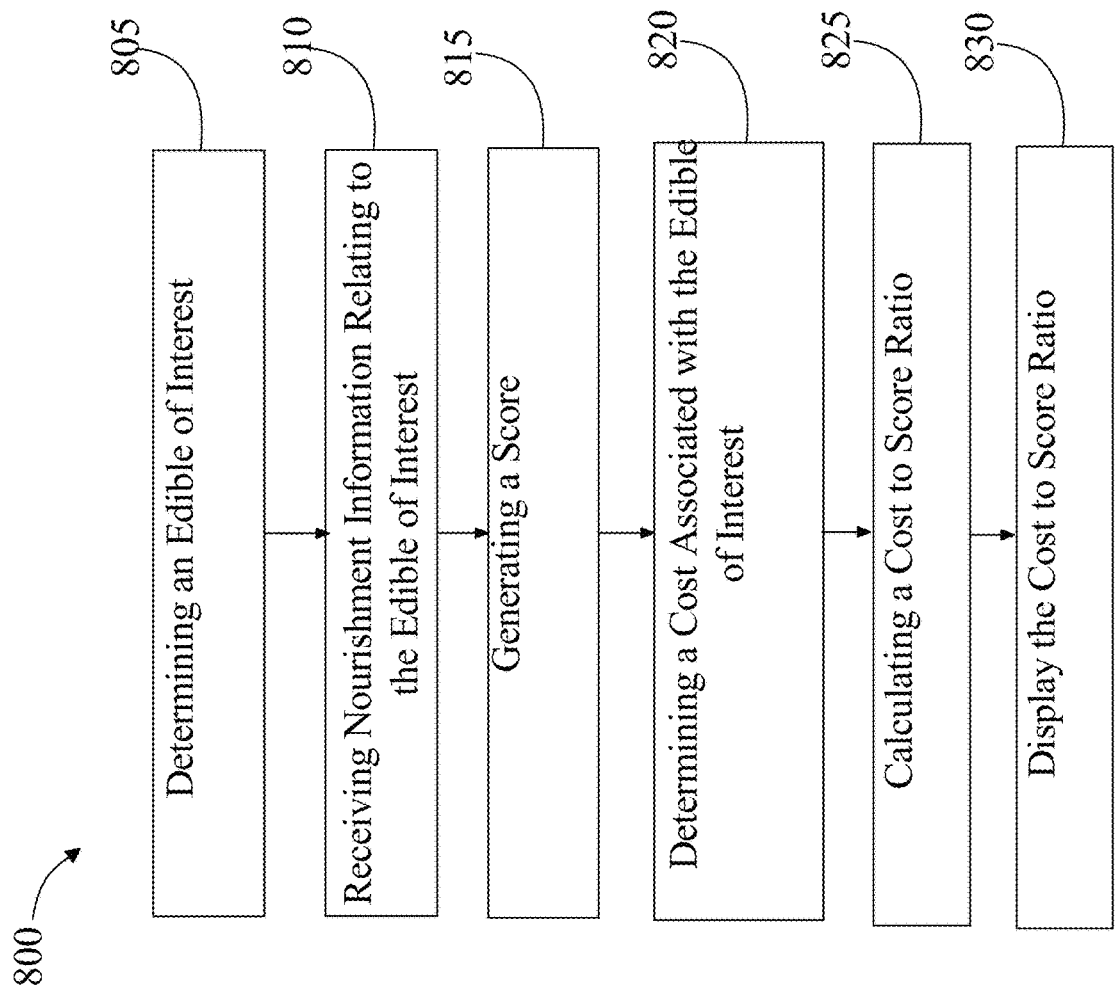
FIG. 8 is a process flow diagram illustrating an exemplary embodiment of a method of calculating an edible score in a display interface.

Referring now to FIG. 8, an exemplary embodiment of a method 800 of calculating a score for an edible in a display interface is illustrated. At step 805, a computing device determines an edible of interest; this may be implemented, without limitation, as described above in reference to FIGS. 1-7. At step 810, computing device receives nourishment information relating to the edible of interest to a user; this may be implemented, without limitation, as described above in reference to FIGS. 1-7.

At step 815, and still referring to FIG. 8, computing device generates a score; this may be implemented, without limitation, as described above in reference to FIGS. 1-7. Generating score includes training a score machine-learning process using edible training data, wherein edible training data contains a plurality of data entries, each data entry containing a performance profile and nourishment information and a correlated score data and generating the score as a function of the score machine-learning process, wherein the score machine-learning process uses the performance profile and the nourishment information relating to the edible of interest as an input, and outputs the score.

Now referring to FIG. 1, computing device may perform machine-learning algorithms using a loss function analysis to select a recommended edible of interest from plurality of candidate edibles of interest. In an embodiment, computing device may compare one or more user specific inputs to a mathematical expression representing a plurality of goal parameters. Mathematical expression may include a linear combination of variables, weighted by coefficients representing relative importance of each goal parameter. For instance, a variable such as food quality, importance to user of organic ingredients versus nonorganic ingredients may be multiplied by a first coefficient representing the importance of organic food standards, a second user input such as total cost may be multiplied by a second coefficient representing the importance of cost, a degree of variance from a and/or classified beneficial ingredient set may be represented as another parameter, which may be multiplied by another coefficient representing the importance of that parameter, a degree of variance from a preference for fresh or frozen ingredients may be multiplied by an additional coefficient representing an importance of that parameter, or the like; persons skilled in the art, upon reviewing the entirety of this disclosure, will be aware of different variables that may be weighted by various coefficients. Use of a linear combination is provided only as an illustrative example; other mathematical expressions may alternatively or additionally be used, including without limitation higher-order polynomial expressions or the like.

Still viewing FIG. 1, mathematical expression may represent a loss function, where a "loss function" is an expression an output of which an optimization algorithm minimizes to generate an optimal result. As a non-limiting example, computing device 104 may calculate variables of set of provider parameters and/or variance of such parameters from goal parameters calculate an output of mathematical expression using the variables and select candidates that produce an output having the lowest size, according to a given definition of "size," of the set of outputs representing each of plurality of edibles of interest; size may, for instance, included absolute value, numerical size, or the like. Selection of different loss functions may result in identification of different edibles of interest as generating minimal outputs; for instance, where organic ingredients are associated in a first loss function with a large coefficient or weight, a candidate edible of interest combination having a small coefficient or weight for organic ingredients may minimize the first loss function, whereas a second loss function wherein organic ingredients has a smaller coefficient but degree of variance from cost goal which has a larger coefficient may produce a minimal output for a different candidate edible of interest having a larger organic ingredients but more closely hewing to a cost goal.

Alternatively or additionally, and still referring to FIG. 1, each candidate edible of interest may be represented by a mathematical expression having the same form as mathematical expression; computing device 104 may compare the former to the latter using an error function representing average difference between the two mathematical expressions. Error function may, as a non-limiting example, be calculated using the average difference between coefficients corresponding to each parameter. A candidate edible of interest having a mathematical expression minimizing the error function may be selected, as representing an optimal expression of relative importance of parameters to a system or user. In an embodiment, error function and loss function calculations may be combined; for instance, a candidate edible of interest resulting in a minimal aggregate expression of error function and loss function, such as a simple addition, arithmetic mean, or the like of the error function with the loss function, may be selected, corresponding to an option that minimizes total variance from goal parameters while simultaneously minimizing a degree of variance from a set of priorities corresponding to goal parameters. Coefficients of mathematical expression and/or loss function may be scaled and/or normalized; this may permit comparison and/or error function calculation to be performed without skewing by varied absolute quantities of numbers.

Still referring to FIG. 1, mathematical expression and/or loss function may be provided by receiving one or more user commands. For instance, and without limitation, a graphical user interface may be provided to user with a set of sliders or other user inputs permitting a user to indicate relative and/or absolute importance of each parameter to the user. Sliders or other inputs may be initialized prior to user entry as equal or may be set to default values based on results of any machine-learning processes or combinations thereof as described in further detail below.

With continued reference to FIG. 1, mathematical expression and/or loss function may be generated using a machine learning to produce loss function, such as without limitation using a regression algorithm. Mathematical expression and/or loss function may be user-specific, using a training set composed of past user selections; mathematical expression and/or loss function may be updated continuously. Mathematical expression and/or loss function may initially be seeded using one or more user entries as above. User may enter a new command changing mathematical expression, and then subsequent user selections may be used to generate a new training set to modify the new expression.

With continued reference to FIG. 1, mathematical expression and/or loss function may be generated using machine learning using a multi-user training set. Training set may be created using data of a cohort of persons having similar demographic, religious, health, and/or lifestyle characteristics to user. This may alternatively or additionally be used to seed a mathematical expression and/or loss function for a user, which may be modified by further machine learning and/or regression using subsequent user selections of candidate edible of interests. Use of regression to derive loss functions, loss function coefficients, and/or mathematical expressions may be performed, without limitation, as described in U.S. Nonprovisional application Ser. No. 16/502,835.

Still referring to FIG. 1, computing device 104 may alternatively or additionally filter edible of interest according to one or more goal parameters and/or user entries. For instance, user may specify a desired meal, and computing device 104 may eliminate edible of interest that does not match the user entry; as further non-limiting examples, edibles of interest that do not match user entries specifying a user maximal price, a maximal wait and/or transport time, or the like may be eliminated as well. Such filtration may be followed by presentation of filtered edible of interest to user, and/or further selection of at least a recommended edible of interest using additional processes such as loss function use as described above.

Figure 9:
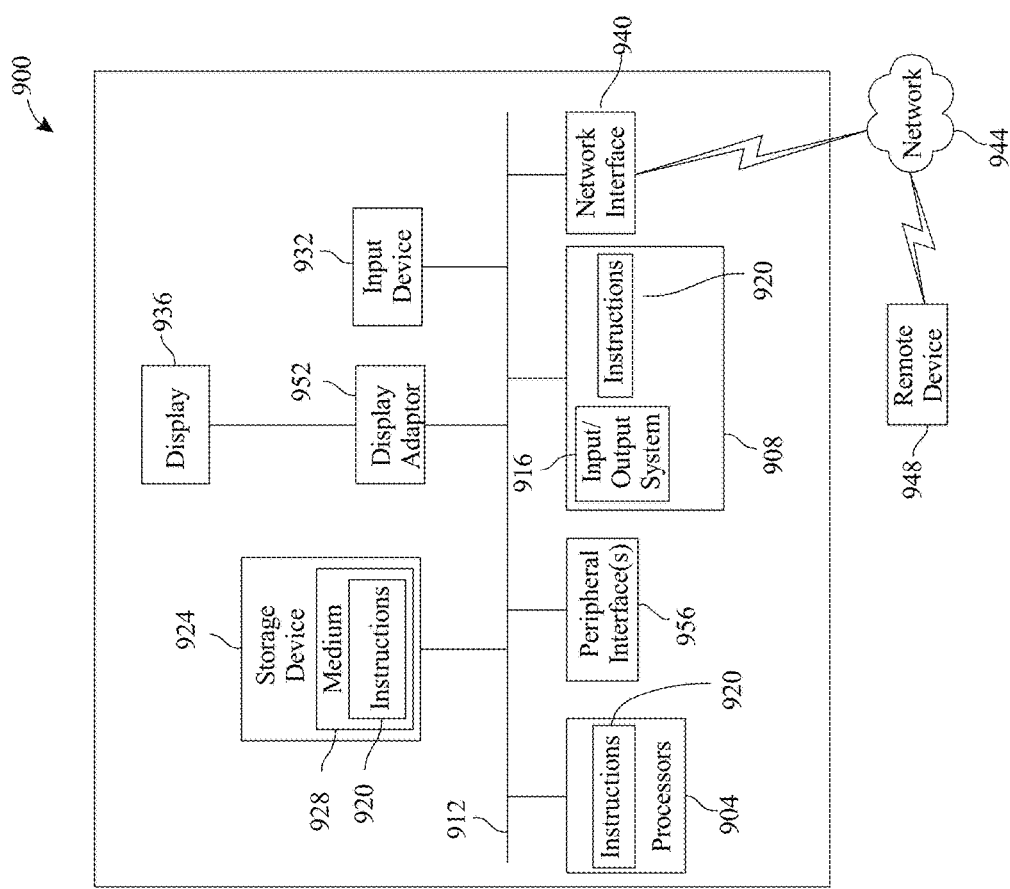
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Memory 908 may include various components (e.g., machine-readable media) including, but not limited to, a random access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for calculating a score for an edible in a display interface, the system comprising:
    a sensor, the sensor configured to detect hematological user data;
    a computing device communicatively connected to the sensor configured to:
    determine an edible of interest relating to a user, wherein determining the edible of interest comprises:
        generating a query wherein the query is configured to search for edibles available within the user's geolocation; and
        identifying a plurality of available edibles within the user's geolocation;
        displaying the plurality of available edibles containing the edible of interest;
    receive nourishment information relating to the edible of interest to the user;
    generate a score, wherein generating the score further comprises:
        training a score machine-learning process using edible training data applied to an input layer of nodes comprising a performance profile input, one or more intermediate layers, and an output layer of nodes comprising a score;
        adjusting one or more connections and one or more weights between nodes in adjacent layers of the score machine-learning model to iteratively update the output layer of nodes by updating the zone strategy training data applied to the input layer of nodes; and
        generating the score as a function of the score machine-learning process, wherein the score machine-learning process uses the performance profile and the nourishment information relating to the edible of interest as an input, and outputs the score;
    determine a cost associated with the edible;
    calculate a cost to score ratio as a function of the cost and the score; and
    display the cost to score ratio within a display interface.

2. The system of claim 1, wherein the computing device is configured to calculate a performance profile associated with the user.

3. The system of claim 2, wherein the performance profile comprises a biological extraction.

4. The system of claim 2, wherein the performance profile comprises a questionnaire.

5. The system of claim 1, wherein the edible of interest is determined as a function of a user dietary habit.

6. The system of claim 1, wherein nourishment information comprises a caloric input.

7. The system of claim 1, wherein nourishment information comprises a nutrient input.

8. The system of claim 1, wherein the computing device is further configured to: generate a dietary classifier, wherein the dietary classifier uses the edible of interest as an input, and outputs a dietary label using a classification process.

9. The system of claim 1, wherein the computing device is further configured to:
    calculate a cost to score ratio for a first edible;
    calculate a second cost to score ratio for a second edible;
    chart the first cost to score ratio as a function of the second cost to score ratio; and
    display the first cost to score ratio as a function of the second cost to score ratio within the display interface.

10. A method of calculating a score for an edible in a display interface, the method comprising:
    a sensor, the sensor configured to detect hematological user data;
    determining an edible of interest relating to a user wherein determining the edible of interest comprises:
        generating a query wherein the query is configured to search for edibles available within the user's geolocation; and
        identifying a plurality of available edibles within the user's geolocation;
        displaying the plurality of available edibles containing the edible of interest;
    receiving nourishment information relating to the edible of interest to a user;
    generating a score, wherein generating the score further comprises:
        training a score machine-learning process using edible training data applied to an input layer of nodes comprising a performance profile input, one or more intermediate layers, and an output layer of nodes comprising a score;
        adjusting one or more connections and one or more weights between nodes in adjacent layers of the score machine-learning model to iteratively update the output layer of nodes by updating the zone strategy training data applied to the input layer of nodes; and
        generating the score as a function of the score machine-learning process, wherein the score machine-learning process uses the performance profile and the nourishment information relating to the edible of interest as an input, and outputs the score;
    determining a cost associated with the edible;
    calculating a cost to score ratio as a function of the cost and the score; and
    displaying the cost to score ratio within a display interface.

11. The method of claim 10 further comprising calculating a performance profile associated with the user.

12. The method of claim 11, wherein the performance profile comprises a biological extraction.

13. The method of claim 11, wherein the performance profile comprises a questionnaire.

14. The method of claim 10, wherein the edible of interest is determined as a function of a user dietary habit.

15. The method of claim 10, wherein nourishment information comprises a caloric input.

16. The method of claim 10, wherein nourishment information comprises a nutrient input.

17. The method of claim 10 further comprising:
generating a dietary classifier, wherein the dietary classifier uses the edible of interest as an input, and outputs a dietary label using a classification process.

18. The method of claim 10 further comprising:
calculating a cost to score ratio for a first edible;
calculating a second cost to score ratio for a second edible;
charting the first cost to score ratio as a function of the second cost to score ratio; and
displaying the first cost to score ratio as a function of the second cost to score ratio within the display interface.

* * * * *